United States Patent [19]

Ueda et al.

[11] Patent Number: 5,429,832
[45] Date of Patent: Jul. 4, 1995

[54] FEED ADDITIVE COMPOSITION FOR RUMINANTS

[75] Inventors: Satoshi Ueda; Haruo Heima; Makoto Ozawa; Takeshi Nagai; Tsuyoshi Nakamatsu; Hiroyuki Sato, all of Kawasaki, Japan

[73] Assignee: Ajinomoto Co., Inc., Tokyo, Japan

[21] Appl. No.: 973,621

[22] Filed: Nov. 9, 1992

[30] Foreign Application Priority Data

Nov. 7, 1991 [JP] Japan .................. 3-291106

[51] Int. Cl.⁶ .................. A23K 1/16; A23K 1/18; A23L 1/30
[52] U.S. Cl. .................. 426/96; 426/2; 426/89; 424/438
[58] Field of Search .................. 426/72, 73, 74, 96, 426/97, 99, 2; 424/438

[56] References Cited

PUBLICATIONS

The Condensed Chemical Dictionary, G. Hawley, 10th Ed., Van Nostrand Reinhold Co., New York, p. 758.
Dialog Data base, File 351 (World Patent Index), Dialog Account No. 89-043825/06, Abstracting Japanese Application 63317052 from Dec. 1988.
Dialog Data base, File 351 (World Patent Index), Dialog Account No. 89-019303/03, Abstracting Japanese Application 63294747 from Dec. 1988.

*Primary Examiner*—Donald E. Czaja
*Assistant Examiner*—Curtis E. Sherrer
*Attorney, Agent, or Firm*—Oblon, Spivak, McClelland, Maier, & Neustadt

[57] ABSTRACT

The present invention provides a feed additive composition for ruminants containing a biologically active substance therein. When administered to ruminants, the composition containing the active substance is stably protected in the rumen while efficient release of the active substance is realized in the abomasum and the following digestive tract. Thus, the released active substance is effectively digested and absorbed by ruminants.

7 Claims, 1 Drawing Sheet

FEED ADDITIVE COMPOSITION FOR RUMINANTS

BACKGROUND OF THE INVENTION

1. Field of the Invention

The present invention relates to a feed additive composition for ruminants. More precisely, it relates to a feed additive composition for ruminants, where a biologically active substance is coated with a coating composition which is stable in the rumen of ruminants and which releases the biologically active substance in the abomasum and the subsequent digestive tract of ruminants.

2. Description of the Background

When biologically active substances such as amino acids or vitamins are directly administered perorally to ruminants such as cattle or sheep, almost all of the substances are decomposed by microorganisms in the rumen of the ruminants which prevents effective absorption of the biologically active substance.

Therefore, rumen by-pass preparations, which protect such biologically active substances in the rumen of ruminants from decomposition by microorganisms so that the substances may be digested in and absorbed in the abomasum and the subsequent digestive tract, are important in the field of feeds, nutrients and animal drugs.

In preparing feed additives for ruminants which contain a biologically active substance, coating of the active substance with a protective substance such as fatty acids and hardened animal and vegetable oils has heretofore been proposed. However, if, a biologically active substance is coated with a sufficient amount of a protective substance so as to protect the active substance in the rumen of ruminants, it is difficult to achieve release of the active substance from the protective substance in the abomasum and the subsequent digestive tract.

In order to overcome the problem, a method has been proposed in which substances other than oils and fats, are added, which may enhance release of the biologically active substance from a protective coating substance. The method involves the dispersal and granulation of the active substance, and to the coating of the biologically active substance with the protective substance containing the additional substances.

For instance, U.S. Pat. No. 4,533,557 describes a method of dispersing a biologically active substance in a mixture comprising at least one member selected from hardened animal oils and fats, hardened vegetable oils and fats and saturated or unsaturated monocarboxylic acids, and chitosan, followed by granulating the dispersion. In the method, chitosan, which may dissolve or swell under acidic conditions, is utilized. However, since the dispersed biologically active substance exists also on the surface of the grains or near the surface thereof, the thickness of the coated layer is not even and some areas of the coated layer are very thin. In general, therefore, the stability of the biologically active substance in the rumen is low. In order to increase stability, the active substance must be coated with a fairly large amount of the protective agent, which, however, adversely diminishes the rate of release of the active substance. In the examples shown in the U.S. patent, the granules which are well protected with a coating, exhibit a poor rate of release of the active substance therefrom, while those which have a high release capacity have a low protecting capability. Anyway, the known granules do not exhibit a satisfactory combination of protection and release characteristics.

Japanese Patent Application Laid-Open No. 60-168351 proposes a method of granulating a biologically active substance along with calcium carbonate in an amount of 20% by weight or more and aliphatic monocarboxylic acids and hardened oils and fats in an amount of 10% by weight or more. In view of the time in which it takes granules to pass through the abomasum of ruminants and in view of the rate of dissolution of calcium carbonate, the release of the active substance still involves some problems.

Japanese Patent Application Laid-Open No. 63-317053 proposes a method of coating a biologically active substance with a coating agent comprising aliphatic monocarboxylic acids, hardened oils and fats, lecithin and glycerin fatty acid esters. However the time in which it takes the coated substance to pass through the small intestines is short and the release of the active substance is not sufficient in view the emulsifying action of lecithin and glycerin fatty acid esters.

In addition, a method of coating a biologically active substance with a pH-responsive synthetic polymer has also been proposed which is based on the difference in the pH value between the rumen and the abomasum. However, in view of the use of an organic solvent for the coating and of the high price of the coating agent, the method cannot be said to be sufficiently satisfactory from the point of view of safety and economics.

SUMMARY OF THE INVENTION

Accordingly, one object of the invention is to provide for a stably protected biologically active substance as a feed additive in the rumen of ruminants.

Briefly, this object and other objects of the present invention as hereinafter will become more readily apparent can be attained in a feed additive composition for ruminants comprising cores each containing a biologically active substance coated with a coating composition containing the following (a), (b) and (c):

(a) at least one substance selected from the group consisting of linear or branched saturated fatty acids having from 14 to 22 carbon atoms, hardened animal oils and fats, hardened vegetable oils and fats, and waxes, (b) chitosan, and (c) at least one substance selected from the group consisting of unsaturated fatty acids and emulsifiers.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
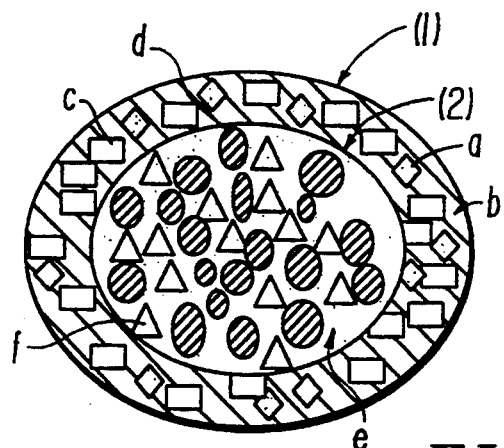
FIG. 1 shows a cross section of the grains prepared in Examples 2.

The present inventors have found that coating of cores containing a biologically active substance with a coating composition containing at least one substance selected from the group consisting of linear or branched saturated fatty acids each having from 14 to 22 carbon atoms, hardened animal oils and fats, hardened vegetable oils and fats and waxes, chitosan and at least one substance selected from the group consisting of unsaturated fatty acids and emulsifiers, in preparing a feed additive composition for ruminants, yields both excellent protection of the biologically active substance in the rumen of ruminants and excellent release of the biologically active substance in the abomasum and the subsequent digestive tract. Such excellent protection and excellent release may be attained further sufficiently by specifically defining the proportions of chitosan and at least one substance selected from the group consisting of unsaturated fatty acids and emulsifiers, the amount of the coating composition, the thickness of the coated layer and the particle size of the coated particle.

The feed additive composition for ruminants of the present invention contains chitosan and at least one substance selected from the group consisting of unsaturated fatty acids and emulsifiers in the coating composition. Chitosan has the property of dissolving or swelling under acid pH conditions and therefore is able to release the active substance from the coated cores under the acidic conditions in the abomasum.

In view of the time in which the coated particles stay in the abomasum, a coating of only chitosan does not provide a sufficient release of active substance. However, in the coating of the present invention, because of the action of the emulsifier such as lecithin, the protective component of oils and fats is emulsified such that the release of the active substance from the coated cores in the small intestines is promoted. Thus, the release of active substance from the present coated particles occurs more efficiently.

The addition of unsaturated fatty acids to the coating composition causes subtle variations of the physical properties such as hardness, strength and melting point of the hardened oils and fats, fatty acids and wax components in the coating composition so that the action of chitosan in the composition may be promoted further, thus assisting the liberation of the active substance from the coated cores.

The amount of the coating composition in the coated particle has an influence on the properties of the coated particle, such as the ability to protect the biologically active substance in the particle in the rumen and the release of the substance from the particles in the abomasum and the following digestive tract. Therefore, the coating composition should fall within the range of from 10 to 60% by weight based on the total weight of the coated particle. If the coating percentage is larger than the range, release of the biologically active substance in the abomasum is less and the content of the active substance in the coated particle is less, though protection of the active substance in the rumen can be improved. Therefore, such a larger coating percentage is unfavorable. If, on the contrary, the coating percentage is lower than the minimum of the range, protection of the active substance in the rumen is not satisfactory.

The thickness of the coating layer should be as even as possible. In order to satisfactorily protect the biologically active substance in the rumen, the thickness should be at least 20 $\mu$m or more. Since the biologically active substance must be released in the abomasum and the following digestive tract, the thickness of the layer should be adjusted to 300 $\mu$m or less.

In order that the feed additive composition for ruminants of the present invention may pass smoothly through the rumen, the specific gravity of the composition should desirably be adjusted to within the range of from 1.0 to 1.5. If the defined specific gravity of the composition cannot be attained by coating the cores with the coating composition as stated above, a specific gravity adjusting agent such as calcium carbonate or talc may be added to the coating composition and/or the core.

The biologically active substance for use in the present invention can be any of a wide variety of substances including nutrients, feeds containing them and medicines, such as amino acids and their derivatives, hydroxy homologue of amino acids, proteins, hydrocarbons, vitamins and veterinary medicines, and mixtures of two or more of these substances.

Specifically, the active substance includes, for example, amino acids such as lysine, methionine, tryptophan and threonine; amino acid derivatives such as N-acylamino acids, N-hydroxymethylmethionine calcium salt and lysine hydrochloride; hydroxy homologs of amino acids such as 2-hydroxy-4-methylmercaptobutyric acid and its salts; powders of natural nutrients such as grain powder, feather powder and fish powder; proteins such as casein, corn protein and potato protein; carbohydrates such as starch, sucrose and glucose; vitamins and substances having the same function as vitamins, such as vitamin A, vitamin A acetate, vitamin A palmitate, vitamin B's, thiamine, thiamine hydrochloride, riboflavin, nicotinic acid, nicotinic acid amide, calcium pantothenate, choline pantothenate, pyridoxine hydrochloride, choline chloride, cyanocobalamine, biotin, folic acid, p-aminobenzoic acid, vitamin D2, vitamin D3 and vitamin E; antibiotics such as tetracyclic antibiotics, amino glycoside antibiotics, macrolide antibiotics and polyether antibiotics; insecticides such as negfon; vermicides such as piperazine; and hormones such as estrogen, stibestrol, hexestrol, thyroprotein and goitrogen.

The method of preparing cores each containing a biologically active substance is not specifically defined. For instance, the cores may be prepared in the form of grains, preferably in the form of nearly spherical particles, by conventional granulation, such as extrusion granulation, fluidized granulation or stirred granulation, optionally with addition of additives such as binder and filler thereto.

As binder, for example, usable are cellulose derivatives such as hydroxypropyl cellulose, methyl cellulose or sodium carboxymethyl cellulose, vinyl derivatives such as polyvinyl alcohol or polyvinyl pyrrolidone, and gum arabic, guaiac gum and sodium polyacrylate.

As filler, for example, usable are starches, proteins and crystalline celluloses.

If desired, calcium carbonate, calcium phosphate, talc and the like may be added to the cores as a specific gravity adjusting agent.

The coating composition which coats the above-mentioned biologically active substance-containing cores contains at least one substance selected from the group consisting of linear or branched saturated fatty acids having from 14 to 22 carbon atoms, hardened animal oils and fats, hardened vegetable oils and fats and waxes, chitosan, and at least one substance selected from the group consisting of unsaturated fatty acids and emulsifiers, and optionally a specific gravity adjusting agent.

At least one substance selected from the group consisting of linear or branched saturated fatty acids having from 14 to 22 carbon atoms, hardened animal oils and fats, hardened vegetable oils and fats and waxes is incorporated into the coating composition for the purpose of protecting the biologically active substance in the cores in the rumen. Therefore, these materials need to be stable at the body temperature of ruminants and have a melting point of 40° C. or higher.

Suitable linear or branched saturated fatty acids having from 14 to 22 carbon atoms, include for example, stearic acid and palmitic acid. Suitable hardened animal oils and fats include hardened beef tallow and hardened lard. As hardened vegetable oils and fats, include hardened oils and fats prepared by hardening palm oil, soybean oil, rapeseed oil, castor oil, and the like. Suitable waxes include carnauba wax and bees wax, as well as natural waxes, synthetic waxes and paraffin wax.

Chitosan for use in the present invention is not specifically defined. It may be any commercial product with an ordinary purity.

Suitable unsaturated fatty acids include, for example, those which have from 10 to 22 carbon atoms such as oleic acid, linoleic acid, linolenic acid, petroselenic acid, palmitoleic acid and ricinoleic acid. A mixture of these ingredients may also be used.

Suitable emulsifiers include, for example, lecithin obtained from: soybeans and egg yolk, and glycerin fatty acid esters, sucrose fatty acid esters and sorbitan fatty acid esters. A mixture of these emulsifiers may also be used. Their purity is not limited.

Suitable specific gravity adjusting agent include, for example, calcium carbonate, talc, calcium phosphate and kaolin.

The amount of chitosan in the coating composition of the present invention normally ranges from 1 to 15% by weight of the total weight of the coating composition; and the component of at least one substance selected from the group consisting of unsaturated fatty acids and emulsifiers normally ranges from 1 to 30% by weight thereto. The optional specific gravity adjusting agent is present in an amount of 10% by weight or less.

If the contents of chitosan, unsaturated fatty acids and emulsifiers in the coating composition are more than the defined ranges in order to increase the rate of release of the biologically active substance from the coated grains it becomes difficult to substantially ensure protection of the active substance. The same applies also to the content of the specific gravity adjusting agent in the composition. That is, if the content of the agent is more than 10% by weight, substantial protection of the active substance is difficult. If, on the contrary, the contents of chitosan, unsaturated fatty acids and emulsifiers in the coating composition are each less than 1% by weight, any such attempt to increase the rate of release of the biologically active substance from the coated particles is diminished, and so that the actual rate of release of the active substance is lower.

Regarding the amount of the component of unsaturated fatty acids and emulsifiers and that of chitosan in the coating composition, suitable proportions of these substances are selected from the respective defined ranges in accordance with the kinds of the unsaturated fatty acids and emulsifiers in order to form a coating layer which is capable of sufficiently protecting the biologically active substance in the rummen and of satisfactorily releasing it in the abomasum and the following digestive tract.

The feed additive composition for ruminants of the present invention is characterized by cores each containing the above-mentioned biologically active substance and coated with the above-described coating composition.

The method of coating the core with the coating composition is not specifically defined and the core may be coated by any conventional coating method. Suitable methods include a fluidized-bed-coating method, a pan coating method and a melt coating method.

Regarding the particle size of the coated particles, if the particle size is too large, the particle may be significantly influenced by mastication of ruminants. If, on the other hand, the particles are too small, coating of the particles by an ordinary method would be difficult. Therefore, the particle size should be adjusted to fall within the range of from 0.5 mm to 5 mm.

The present invention will be explained in more detail by way of the following examples and comparative examples which, however, are not intended to restrict the scope of the present invention.

EXAMPLES

The effectiveness of the feed additive composition for ruminants of the present invention is evaluated by the methods described below. Protection Test (Protection Of Active Substance in Rumen):

About one g of a sample prepared is placed in a 200 ml-Erlenmeyer flask, and 100 ml of McDougall buffer solution corresponding to rumen juice is added thereto and shaken at 39° C. for 24 hours. After shaking is stopped, the amount of the biologically active substance which dissolves in the buffer is analyzed, and the dissolving property of the substance in the rumen is calculated.

The amount of the biologically active substance, which is an amino acid mentioned below, which dissolves in the test is determined by liquid chromatography analysis.

McDougall buffer solution is a buffer prepared by dissolving the following chemicals in 1000 ml of water.

| Sodium Hydrogencarbonate | 7.43 g |
|---|---|
| Disodium Phosphate 12-hydrate | 7.00 g |
| Sodium Chloride | 0.34 g |
| Potassium Chloride | 0.43 g |
| Magnesium Chloride 6-hydrate | 0.10 g |
| Calcium Chloride | 0.05 g |

Release Test (Release of Active Substance in Abomasum):

After finish of the preceding protection test, the shaken sample is recovered and placed in a 200 ml-Erlenmeyer flask. 40 ml of Clark-Lub's buffer corresponding to abomasum juice is added thereto and shaken at 39° C. for one hour. After shaking is stopped, the amount of the biologically active substance which dissolves into the buffer is analyzed, whereby the dissolving property of the substance in the abomasum is calculated.

Clark-Lub's buffer is a buffer prepared by dissolving the following chemicals in 1000 ml of water.

| Potassium Chloride | 3.73 g |
|---|---|
| Hydrochloric Acid | 2.1 ml |

Release Test (Release of Active Substance in Small Intestines):

After completion of the preceding Release-in-Abomasum test, the shaken sample is recovered and put in a 200 ml-Erlenmeyer flask. 100 ml of a buffer corresponding to small intestinal juice is added thereto and shaken at 39° C. for 7 hours. After shaking is stopped, the amount of the biologically active substance which dissolves into the buffer is analyzed, whereby the dissolving property of the substance in small intestines is calculated. Preparation of Cores Containing Biologically Active Substance weight of the cores (A) prepared above were coated with 67 parts by weight of the coating composition (coating ratio 40%). The coating is effected with a stirring fluidized granulating and coating machine (New Marumerizer, manufactured by Fuji Powdal Co.). The thus coated particles are tested by the above-mentioned test methods to obtain the percentage of the active substance which dissolves in the rumen, the percentage which dissolves in the rumen and the percentage which dissolves in the small intestines. The results obtained are shown in Table 1 below.

TABLE 1

| Example | 1 | 2 | 3 | 4 | 5 | 6 | 7 | 8 | 9 | 10 | 11 | 12 |
|---|---|---|---|---|---|---|---|---|---|---|---|---|
| Biologically Active Substance | (A) | (A) | (A) | (A) | (A) | (A) | (A) | (A) | (B) | (B) | (B) | (B) |
| Core (parts by weight) | 100 | 100 | 100 | 100 | 100 | 100 | 100 | 100 | 100 | 100 | 100 | 100 |
| Coating Composition (parts by weight) | 67 | 43 | 33 | 67 | 43 | 25 | 33 | 54 | 25 | 43 | 43 | 33 |
| Composition of Coating Layer | | | | | | | | | | | | |
| Hardened Beef Tallow | 85 | 85 | 83 | 85 | 85 | 93 | 83 | 85 | 89 | 85 | 70 | 81 |
| Chitosan | 10 | 5 | 10 | 10 | 5 | 2 | 2 | 5 | 1 | 10 | 15 | 10 |
| Oleic Acid | 5 | 5 | 2 | — | — | — | — | 5 | 10 | — | — | 2 |
| Lecithin | — | — | — | 5 | 5 | 5 | 10 | 5 | — | 5 | 15 | 2 |
| Calcium Carbonate | — | 5 | 5 | — | 5 | 2 | 5 | — | — | — | — | 5 |
| Percentage of Release (%) | | | | | | | | | | | | |
| in buffer corresponding to rumen | 5 | 14 | 26 | 17 | 29 | 32 | 23 | 18 | 19 | 12 | 21 | 18 |
| in buffer corresponding to abomasum | 2 | 1 | 1 | 6 | 1 | 1 | 1 | 2 | 0 | 3 | 8 | 2 |
| in buffer corresponding to small intestines | 80 | 54 | 53 | 63 | 65 | 62 | 50 | 62 | 71 | 55 | 56 | 60 | cally Active Substance 325 g of L-lysine hydrochloride (A), 172.5 g of talc, 2.5 g of sodium carboxymethyl cellulose and 135 g of water are placed into and kneaded in a kneader. The kneaded mix is then pelletized with an extrusion pelletizer having a 1.5 mm-mesh screen (Fine Disc Pelleter, manufactured by Fuji Powdal Co.) into cylindrical pellets. The pellets thus obtained are formed into nearly spherical granules with a spherical granule producing machine (Marumerizer-manufactured by Fuji Powdal Co.). After the thus obtained spherical granule are dried by fluidized drying, they are sieved into 1.4 mm to 1.7 mm granules (cores) each containing L-lysine hydrochloride. In the same manner, 1.4 mm to 1.7 mm cores, each containing D,L-methionine, are obtained from 375 g of D,L-methionine (B), 120 g of talc, 5 g of sodium carboxymethyl cellulose and 150 g of water.

Example 1

10 parts by weight of chitosan and 5 parts by weight of oleic acid are added to and mixed with 85 parts by weight of molten hardened beef tallow (melting pointy 61° C.) to prepare a coating composition. 100 parts by Examples 2 to 12

Other coated particles are prepared in the same manner as, described in Example 1, except that the coating compositions as indicated in Table I above are used. The particles are tested in the same manner and the results obtained are shown in Table 1. FIG. 1 shows a cross section of the coated particles as prepared in Example 2.

Comparative Examples 1 to 8

Comparative coated particles are prepared in the same manner as described in Example 1, except that the coating compositions as indicated in Table 2 below are used.

FIG. 1 is a scheme of the feed additive composition particles for ruminants of this invention, Each component of the composition is as follows;
(1) Coating Composition a; CaCO₃ b; Hardened Beef Tallow+Oleic Acid c; Chitosan
(2) Core d; Lys-HCl e; Sodium Carboxymethyl Cellulose f; Talc

TABLE 2

| Comparative Example | 1 | 2 | 3 | 4 | 5 | 6 | 7 | 8 |
|---|---|---|---|---|---|---|---|---|
| Biologically Active Substance | (A) | (A) | (A) | (A) | (B) | (B) | (B) | (A) |
| Core (parts by weight) | 100 | 100 | 100 | 100 | 100 | 100 | 100 | 100 |
| Coating Composition (parts by weight) | 67 | 67 | 100 | 43 | 43 | 100 | 25 | 11 |
| Composition of Coating Layer | | | | | | | | |
| Hardened Beef Tallow | 90 | 70 | 60 | 95 | 95 | 60 | 90 | 85 |
| Chitosan | 10 | 20 | 5 | — | 5 | 5 | — | 10 |
| Oleic Acid | — | 5 | 35 | — | — | — | 10 | 5 |
| Lecithin | — | — | — | 5 | — | 35 | — | — |
| Calcium Carbonate | — | 5 | — | — | — | — | — | — |
| Thickness of Coating Layer (μm) | — | — | — | — | — | — | — | 15 |
| Percentage of Release (%) | | | | | | | | |
| in buffer corresponding to rumen | 31 | 100 | 100 | 8 | 11 | 100 | 12 | 100 |
| in buffer corresponding to abomasum | 0 | — | — | 0 | 0 | — | 0 | — |
| in buffer corresponding to small intestines | 29 | — | — | 3 | 3 | — | 8 | — |

Comparative Example 9

The example of U.S. Pat. No. 4,533,557 is carried out for the purpose of confirming the protection of the biologically active substance in the rumen, in which the active substance is dispersed in a coating composition containing chitosan and is granulated.

Figure 2:
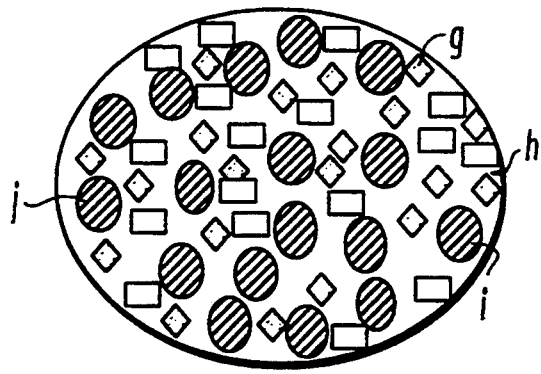
FIG. 2 is a cross section of the grains prepared in Comparative Example 9.

Precisely, 57 parts by weight of molten stearic acid, 3 parts by weight of chitosan as passed through a 213 μm sieve, 10 parts by weight of calcium carbonate and 30 parts by weight of lysine hydrochloride as ground into a particle size of 75 μm or less are blended, and the resulting mix is dropped onto a cooled stainless steel vat to obtain semi-spherical particles. The coated particles are tested and the results obtained are shown in Table 3 below. FIG. 2 shows a cross section of the coated grain of Comparative Example 9.

FIG. 2 is a scheme of the feed additive composition particle for ruminants prepared by the process of the example of U.S. Pat. No. 4,533,557. Each component of the composition is as follows;

g; CaCO₃ h; Stearic Acid i; Chitosan j; Lys-HCl

TABLE 3

| Comparative Example | 9 | 10 |
|---|---|---|
| Biologically Active Substance | (A) | (B) |
| Grain Composition (%) | | |
| Lysine Hydrochloride | 30 | 30 |
| Stearic Acid | 57 | — |
| Hardened Beef Tallow | — | 48 |
| Chitosan | 3 | 2 |
| Calcium Carbonate | 10 | 20 |
| Liberation (%) | | |
| in buffer corresponding to rumen fluid | 100 | 84 |
| in buffer corresponding to abomasum fluid | — | 0 |
| in buffer corresponding to small intestine fluid | | 12 |

Comparative Example 10

Comparative coated grains are prepared in the same manner as described in comparative Example 9, except that the composition as indicated in Table 3 above is used. The particles are tested in the same manner and the results obtained are shown in Table 3.

From the above-mentioned results, it is understood that the feed additive composition samples of the present invention more effectively protect the biologically active substance in the rumen and more effectively release it in the abomasum and the subsequent digestive tract, than the comparative composition samples.

Advantage of the Invention

As explained in detail above, coating cores each containing a biologically active substance with a coating composition containing at least one substance selected from the group consisting of linear or branched saturated fatty acids having from 14 to 22 carbon atoms, hardened animal oils and fats, hardened vegetable oils and fats and waxes, chitosan and at least one substance selected from the group consisting of unsaturated fatty acids and emulsifiers, in accordance with the present invention produces a feed additive composition for ruminants. The present product yields both excellent protection of the biologically active substance in the rumen of ruminants and excellent release of the substance in the abomasum and the following digestive tract, exceeding the capabilities of known technical formulations. Such excellent protection and excellent release are sufficiently established by specifically defining the proportions of chitosan and at least one substance selected from the group consisting of unsaturated fatty acids and emulsifiers, the amount of the coating composition, the thickness of the coated layer and the grain size of the coated grains.

Thus, the present invention provides a feed additive composition containing a biologically active substance therein and when the composition is administered to ruminants, the active substance may effectively be absorbed by the ruminants. The industrial importance of the present invention is significant.

What is claimed is:

1. A feed additive composition for ruminants, which comprises: cores each containing a biologically active substance coated with a coating composition containing the following (a), (b) and (c):
   (a) at least one substance selected from the group consisting of linear or branched saturated fatty acids having from 14 to 22 carbon atoms, hardened animal oils and fats, hardened vegetable oils and fats, and waxes,
   (b) chitosan, and
   (c) oleic acid and emulsifiers.

2. The feed additive composition for ruminants as claimed in claim 1, in which the amount of chitosan in the coating composition is from 1 to 15% by weight to the total coating composition, and the total amount of oleic acid and emulsifiers is from 1 to 15% by weight of the total coating composition.

3. The feed additive composition for ruminants as claimed in claim 1, wherein the emulsifier of component (c) is lecithin.

4. The feed additive composition for ruminants as claimed in claim 1, in which the amount of the coating composition is from 10 to 60% by weight of the total coated particles.

5. The feed additive composition for ruminants as claimed in claim 1, in which the thickness of the coating composition on the cores each containing a biologically active substance is from 20 μm to 300 μm.

6. The feed additive composition for ruminants as claimed in claim 1, in which the particle size of the coated particles is from 0.5 to 5 mm.

7. The feed additive composition for ruminants as claimed in claim 1, wherein said component (a) has a melting point of 40° C. or higher.

* * * * *